(12) United States Patent
Thiel et al.

(10) Patent No.: US 11,518,752 B2
(45) Date of Patent: Dec. 6, 2022

(54) PROCESS FOR THE PURIFICATION OF ORGANIC SULFUR COMPOUNDS

(71) Applicant: BASF SE, Ludwigshafen am Rhein (DE)

(72) Inventors: Indre Thiel, Ludwigshafen am Rhein (DE); Thomas Maximilian Wurm, Ludwigshafen am Rhein (DE); Peter Rudolf, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/634,473

(22) PCT Filed: Aug. 13, 2020

(86) PCT No.: PCT/EP2020/072722
§ 371 (c)(1),
(2) Date: Feb. 10, 2022

(87) PCT Pub. No.: WO2021/028522
PCT Pub. Date: Feb. 18, 2021

(65) Prior Publication Data
US 2022/0267293 A1    Aug. 25, 2022

(30) Foreign Application Priority Data
Aug. 14, 2019  (EP) .................................... 19191798

(51) Int. Cl.
*C07D 327/04*  (2006.01)
(52) U.S. Cl.
CPC .................. *C07D 327/04* (2013.01)
(58) Field of Classification Search
CPC .................................................. C07D 327/04
See application file for complete search history.

(56) References Cited

U.S. PATENT DOCUMENTS

2002/0082168 A1    6/2002   Graham et al.

FOREIGN PATENT DOCUMENTS

| DE | 10129306 A1 | 12/2002 |
|---|---|---|
| WO | 02/48032 | 6/2002 |
| WO | WO-2019/034469 A1 | 2/2019 |

OTHER PUBLICATIONS

Nehlsen et al., Ind. Eng. Chem. Res. (2003), 42, 26, 6919-6923.*
Zhao et al. Preparation of odour removal catalysts with self-regeneration capability. Appl Petrochem Res 6, 191-199 (2016).*
International Preliminary Report on Patentability dated Feb. 8, 2022 in PCT/EP2020/072722, 6 pages.
Kaplan Bekaroglu, et al., "Hybrid Adsorptive and Oxidative Removal of Natural Organic Matter Using Iron Oxide-Coated Pumice Particles", Journal of Chemistry, vol. 2016, Article ID 3108034, Mar. 29, 2016, pp. 1-8.
International Search Report dated Nov. 13, 2020 in PCT/EP2020/072722, 3 pages.
Written Opinion dated Nov. 13, 2020 in PCT/EP2020/072722, 4 pages.

* cited by examiner

*Primary Examiner* — Valerie Rodriguez-Garcia
(74) *Attorney, Agent, or Firm* — Grüneberg and Myers PLLC

(57) ABSTRACT

A process for the purification of organic sulfur compounds involves bringing the organic sulfur compounds, in a liquid phase, into contact with an oxide of a metal from groups VIIb or VIIIb and an oxide of a metal from groups Ia to IIIa of the periodic system, or alternatively, with a mixed-oxide thereof; for a contact period of at least 1 minute. Afterwards, the oxides and the organic sulfur compounds are separated.

9 Claims, No Drawings

PROCESS FOR THE PURIFICATION OF ORGANIC SULFUR COMPOUNDS

CROSS-REFERENCE TO RELATED APPLICATIONS

This application is the National Stage entry under § 371 of International Application No. PCT/EP2020/072722, filed on Aug. 13, 2020, and which claims the benefit of priority to European Application No. 19191798.8, filed on Aug. 14, 2019. The content of each of these applications is hereby incorporated by reference in its entirety.

BACKGROUND OF THE INVENTION

Field of the Invention

Object of the invention is a process for the purification of organic sulfur compounds, wherein
the organic sulfur compounds are in a liquid phase and are brought into contact with an oxide of a metal from groups VIIb or VIIIb and an oxide of a metal from groups Ia to IIIa of the periodic system or, alternatively, a mixed-oxide thereof
for a contact period of at least 1 minute, and
the oxides and the organic sulfur compounds are separated thereafter.

Description of Related Art

Organic sulfur compounds are valuable compounds with various desired properties caused by the content of sulfur. They may be obtained by chemical reactions involving the use of mercaptanes, sulfur or sulfides as reactants.

However, the organic sulfur compounds obtained often have bad odor which is due to a content of undesired by-products which probably comprise sulfur in form of mercapto groups or any unreacted starting materials with sulfur atoms.

An example of organic sulfur compounds are cyclic monothiocarbonates. A suitable synthesis for cyclic monothiocarbonates is described in WO 2019/034469 A1. However, the monothiocarbonates obtained have an unpleasant or nasty smell caused by sulfur comprising by-products.

US 2002/0082168 A1 discloses an activated carbon-metal oxide matrix for the removal of odorous compounds from a gas. The use of iron oxide particles as adsorbent is known from DE 10129306 A1. Sehnaz Sule Kaplan Bekaroglu et al. describe in Journal of Chemistry, vol. 2016, article ID 3108034, http://dx.doi.org/10.1155/2016/3108034, an adsorptive and oxidative removal of natural organic matter from water using iron oxide coated pumice. The prior art does not disclose the purification or reduction of odor of systems wherein both, the product to be purified and the by-product to be removed comprise sulfur.

It is an object of this invention to provide an easy and economic process for the purification of organic sulfur compounds which results in organic sulfur compounds with reduced odor.

SUMMARY OF THE INVENTION

It has now been found that organic sulfur compounds having reduced odor may be obtained by a process using specific metal oxides.

Accordingly, the invention relates to a process for the purification of organic sulfur compounds, wherein
the organic sulfur compounds are in a liquid phase and are brought into contact with an oxide of a metal from groups VIIb or VIIIb and an oxide of a metal from groups Ia to IIIa of the periodic system or, alternatively, a mixed-oxide thereof
for a contact period of at least 1 minute, and
the oxides and the organic sulfur compounds are separated thereafter.

DETAILED DESCRIPTION OF THE INVENTION

To the Organic Sulfur Compounds

Organic sulfur compounds are preferably compounds with a molecular weight of at maximum 5.000 g/mol, more preferably of at maximum 1000 g/mol and most preferably of at maximum 500 g/mol.

The organic sulfur compounds may be aliphatic or aromatic compounds. They may comprise more than one sulfur atom, for example. Preferably, they comprise 1 to 10, more preferably 1 to 5 and most preferably 1 to 3 sulfur atoms.

The sulfur atom may, for example, be part of a thioether group or a ring system comprising one or two, preferably one sulfur atom, the ring system may be a five to eight membered ring, whereby the ring forming atoms may be substituted.

Preferably, the organic sulfur compounds are part of such a ring system.

Particularly preferred organic sulfur compounds are compounds with at least one five-membered cyclic monothiocarbonate group, shortly referred to as "monothiocarbonate compounds".

Any reference to "monothiocarbonate compounds" shall include mixtures of different monothiocarbonate compounds, if not otherwise mentioned or obvious from the context.

A five-membered cyclic monothiocarbonate group is preferably a ring system with 5 members, three of them are from the monothiocarbonate —O—C(=O)—S— and the further two members are carbon atoms closing the five-membered cycle.

The monothiocarbonate compounds may comprise, for example, up to 1000, in particular up to 500, preferably up to 100 five-membered cyclic monothiocarbonate groups. In a preferred embodiment the monothiocarbonate compounds comprise 1 to 10, notably 1 to 5 five-membered cyclic monothiocarbonate groups. In a most preferred embodiment the monothiocarbonate compounds comprise 1 to 3, particularly 1 or 2 five-membered cyclic monothiocarbonate groups.

The monothiocarbonate compounds may have, for example, a molecular weight of up to 500.000 g/mol. Preferred monothiocarbonate compounds have a molecular weight of at maximum 5000 g/mol, more preferably of at maximum 1000 g/mol. Most preferred monothiocarbonate compounds have a molecular weight of at maximum to 500 g/mol.

In a preferred embodiment the monothiocarbonate compounds do not comprise any primary or secondary amino groups.

In a particularly preferred embodiment, the monothiocarbonate compounds do not comprise other functional groups than monothiocarbonate groups, carboxylic ester groups or ether groups.

Suitable monothiocarbonate compounds with one five-membered cyclic monothiocarbonate group are disclosed in WO 2019/034470 A1. Preferred monothiocarbonate compounds with one five-membered cyclic monothiocarbonate group are compounds of formula (I)

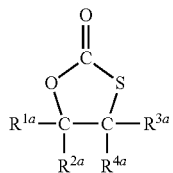

with $R^{1a}$ to $R^{4a}$ independently from each other representing hydrogen or an organic group with up to 50 carbon atoms whereby, alternatively, $R^{2a}$, $R^{4a}$ and the two carbon atoms of the monthiocarbonate group may also together form a five to ten membered carbon ring.

Suitable monothiocarbonate compounds with more than one five-membered cyclic monothiocarbonate group are, for example, disclosed in WO 2019/034473 A1. Preferred monothiocarbonate compounds with more than one five-membered cyclic monothiocarbonate group are compounds of formula (II)

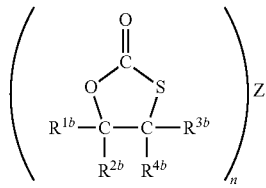

with $R^{1b}$ to $R^{4b}$ independently from each other representing hydrogen or an organic group with up to 50 carbon atoms, whereby, alternatively, $R^{2b}$, $R^{4b}$ and the two carbon atoms of the monothiocarbonate group may also together form a five to ten membered carbon ring and one of the groups $R^{1b}$ to $R^{4b}$ is a linking group to Z, n representing an integral number of at least 2, and Z representing a n-valent organic group.

Various processes are known for the preparation of monothiocarbonate compounds.

According to U.S. Pat. Nos. 3,072,676 and 3,201,416 ethylene monothiocarbonates may be prepared by a two-step-process. In a first step mercaptoethanol and chlorocarboxylates are reacted to give hydroxyethylthiocarbonate, which is heated in the second step in the presence of a metal salt catalyst to the ethylene monothiocarbonate.

According U.S. Pat. No. 3,517,029 alkylene monothiocarbonates are obtained by reacting mercaptoethanol and a carbonate diester in the presence of a catalytically active salt of thorium.

According to the process disclosed in U.S. Pat. No. 3,349,100 alkylene monothiocarbonates are obtained by reacting an epoxide with carbonyl sulfide.

A synthesis using phosgene as starting material is known from U.S. Pat. No. 2,828,318. Phosgene is reacted with hydroxymercaptanes.

Preferably, the monothiocarbonate compounds used in the process for the purification as defined above are compounds that are obtained as product from a process comprising reacting a compound with at least one epoxy group or at least one halohydrin group with phosgene or an alkylformate to give an adduct, and then reacting the adduct with a compound comprising anionic sulfur, optionally followed by a further work-up of the obtained crude product by extraction or distillation.

The above process is disclosed in WO 2019/034469 A1 (first step reaction with epoxy compound) and in PCT patent application with application no. PCT/EP2020/051110 (first step reaction with halohydrin).

The monothiocarbonate compounds obtained usually comprise by-products with a content of sulfur. Such by-products cause a very nasty smell. Often such by-products cannot be totally removed by a standard work-up involving process steps such as distillation or one or more extractions, which are notably extractions with $NaHCO_3$. The odor of the monothiocarbonate compounds is usually still bad after such standard work-up.

The organic sulfur compounds, notably monothiocarbonate compounds used for the process are in a liquid phase.

The monothiocarbonate compounds obtained from the above preparation process may be liquid or solid at 21° C., 1 bar.

Monothiocarbonate compounds that are liquid at 21° C., 1 bar may be used as such, without solvent.

Monothiocarbonate compounds that are solid at 21° C., 1 bar are preferably used in form of a solution.

Suitable solvents for solid monothiocarbonate compounds are notably aprotic solvents.

The aprotic solvents may be hydrophobic, such as, for example, hydrocarbons, including aromatic hydrocarbons and chlorinated hydrocarbons, for example, toluene, chlorobenzene or dichloro-benzene, chloroform, or hydrophilic solvents such as, for example, acetonitrile or dimethyl sulfoxide or esters or ethers like tetrahydrofuran, dioxane, polyether or glymes.

To the Oxides

The organic sulfur compounds are brought into contact with two different oxides as defined above or with a mixed-oxide thereof.

In the first alternative, the contact is with an oxide of a metal from groups VIIb or VIIIb and, in addition, with an oxide of a metal from groups Ia to IIIa of the periodic system.

Preferably, the oxide of a metal from groups VIIb or VIIIb is an oxide of iron, cobalt or nickel or a mixture thereof.

Most preferably, the oxide of a metal from groups VIIb or VIIIb is an iron oxide, particularly an iron oxide wherein the iron has an oxidation degree of at least 3; a most preferred iron oxide is $Fe_2O_3$.

Preferably, the oxide of a metal from groups Ia to IIIa is an oxide of an alkali or earth alkali metal, or an oxide of alumina.

More preferably, the oxide of a metal from groups Ia to IIIa is sodium oxide ($Na_2O$) or potassium oxide ($K_2O$); most preferably it is potassium oxide.

The oxides from the metals of groups VIIb or VIIIb and of Ia to IIIa of the periodic system may be used separately or in form of mixtures. The oxides may also be used in sequence, if the process is performed continuously.

In the second alternative, the contact is with a mixed-oxide of the above-mentioned oxides. The preferred embodiments regarding the metals correspond to those of the first alternative.

Mixed-oxides are well known in the field of catalysts. Mixed-oxides are used as unsupported catalysts in various processes. The mixed-oxides may be obtained by melting or sintering mixtures of the respective metal oxides. In such processes other components, notably other metal oxides may be used.

In a preferred embodiment, the mixed-oxide for the process of this invention is formed to at least 50% by weight, more preferably to at least 70% by weight and most preferably to at least 90% by weight from oxides of a metal from groups VIIb or VIIIb and oxides of a metal from groups Ia to IIIa of the periodic system, only. That is, the mixed-metal oxide is formed to at least 50% by weight from oxides of a metal from groups VIIb or VIIIb, more preferably to at least 70% by weight and most preferably to at least 90% by weight.

Commercially available catalysts comprising the respective metal oxides or mixed-oxides may be used for the process of this invention. Such catalysts are known, for example, for dehydrogenation processes. For the process of this invention catalysts that have been removed from a dehydrogenation reactor after a long term of operation may be used with or without any regeneration.

Suitable examples of mixed-oxides are, for example, $KFeO_2$, $K-Mn_3O_4$, $K-Fe_3O_4$, $KMn_4O_8$, $KMn_8O_{16}$, and $K_2Fe_{22}O_{34}$.

The metal oxides or mixed-oxide used in the process may be regenerated and then be used in other processes such as catalytic processes or may be re-used in the process of the invention itself.

In a most preferred embodiment of the invention, a mixed-oxide is used.

The above oxides or the mixed-oxide are preferably used in form of molded bodies, notably of molded bodies may be obtained from extrusion or tableting.

To the Process

The general term "oxides" as used below shall include the mixed-oxide, if not expressly stated or obvious from the context otherwise.

The oxides may be brought into contact with the organic sulfur compounds in any suitable manner.

The process of this invention may be a batch process, a semi-continuous process or a continuous process. In a continuous process all starting materials are fed continuously to the reactor and all products are removed continuously, whereby the oxides may be separated from the product streams by usual means, such as distillation, filtration or precipitation, as the case may be.

In a preferred embodiment, the process is a batch process. In such batch process the oxides are added to the organic sulfur compounds which are in the liquid phase.

In the batch process the oxides are preferably used in a total amount of 0.05 to 1 part by weight per 1 part by weight of the organic sulfur compounds, which are notably the monothiocarbonate compounds.

In a continuous process the oxides are preferably used in form of a fixed bed which is installed in a reactor. A continuous flow of organic sulfur compounds passes through the fixed bed.

The contact of the organic sulfur compounds and the oxides is preferably at 10 to 150° C., more preferably at 20 to 100° C., particularly at 20 to 50° C. and most preferably at 20 to 35° C.

The contact period is preferably from 5 minutes to 12 hours, more preferably from 10 minutes to 8 hours, particularly from 30 minutes to 5 hours and most preferably from 30 minutes to 3 hours.

After the contact period, the oxides and the organic sulfur compounds, which are notably monothiocarbonate compounds, are separated, for example, by filtration.

Any solvents used in combination with the organic sulfur compounds compounds, respectively monothiocarbonate compounds, may be removed, for example, by distillation.

The organic sulfur compounds, respectively the monthiocarbonate compounds, obtained from the process have a significantly reduced odor.

EXAMPLES

Synthesis of 5-[4-[(2-oxo-1,3-oxathiolan-5-yl)methoxy]butoxymethyl]-1,3-oxathiolan-2-one of Formula

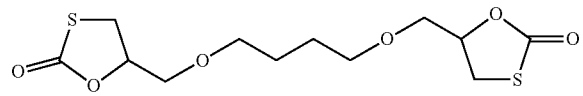

which is shortly referred to as butanediol-dithiocarbonate or BDO-TC.

The synthesis was made according to the process disclosed in WO 2019/034469 A1.

In the first step of the synthesis, the epoxide 1,4 butanediol diglycidylether was reacted with phosgene as described in WO 2019/034469 A1.

In the second step, the obtained β-chloroalkyl chloroformate ([2-chloro-1-[4-(3-chloro-2-chlorocarbonyloxypropoxy)butoxymethyl]ethyl] carbonochloridate) (845 g, 2.1 mol) and dichloromethane (2.5 L) were placed in a 8 liter reactor. The solution was cooled down to 0° C. before $Na_2S$ (2.2 eq., 15 wt % aqueous solution) was slowly added, maintaining the temperature at 5° C. After the complete addition the reaction mixture was allowed to warm to room temperature and stirred for 1 hour. The phases were separated, and the aqueous phase was extracted with dichloromethane (1×0.5 L). The combined organic phase was extracted with water (3×0.5 L), dried over $Na_2SO_4$ and filtered over Celite 545 (300 g per kg initial chloroformiate). The solvent was removed from the organic phase under reduced pressure, and the desired product was obtained as a clear viscous liquid (656 g, 96%).

The above synthesis was made for two different grades of 1,4-butanediol-diglycidylether.

One grade is a relatively pure grade with a minor content of other epoxides, notably epoxides of higher molecular weight.

The other grade was a technical grade comprising a significant content of other epoxides.

Accordingly, two different products were obtained from the synthesis.

One product, referred to as "pure BDO-TC", having a content of BDO-TC of 84.2 area %, measured by gas chromatography.

A second product, referred to as "technical BDO-TC", having a content of BDO-TC of 61.3 area %, measured by gas chromatography.

Purification Examples 1 to 13

The respective BDO-TC (5 g) was dissolved in toluene (10 g), and the additive (see table) was added in an amount of 5 parts by weight, based on 100 parts by weight of the solution. The temperature was at 25° C. The solution was stirred for 2 hours before the additive was filtered off. All volatiles and toluene were removed from the organic phase under reduced pressure, yielding the BDO-TC as a viscous liquid.

Testing

The odor of the BDO-TC obtained was tested immediately thereafter. The samples were tested at room temperature by 3 different people. The participants reported their olfactoral assessment according to the following classification scheme:

The odor was judged pursuant to a scale from 1 to 5.
1: odorless
2: slight stale odor
3: slight "mercaptan odor"
4: "mercaptan odor"
5: distinct "mercaptan odor"

Before the treatment with the additive, the pure BDO-TC had an odor of classification 4

Before the treatment with the additive, the technical BDO-TC had an odor of classification 5.

The results for different additives are shown in the Table below.

TABLE

Purification/deodorization of BDO-CTC with various additives

| Exp. | BDO-TC | Additive | Color after treatment | Odor |
|---|---|---|---|---|
| 1 | "pure" | S6-62 (pressed wires) | clear liquid | 2 |
| 2 | technical | S6-62 (pressed wires) | clear liquid | 2 |
| 3 | "pure" | NIO (Fe$_2$O$_3$) (powder) | red liquid | 4 |
| 4 | technical | NIO (Fe$_2$O$_3$) (powder) | red liquid | 4 |
| 5 | technical | SiO$_2$ (Supelco) | clear liquid | 3 |
| 6 | "pure" | Ambersept 900 (water wet) | clear liquid | 4 |
| 7 | technical | Ambersept 900 (water wet) | clear liquid | 4 |
| 8 | "pure" | Selexsorb COS BASF | clear liquid | 3 |
| 9 | technical | Selexsorb COS BASF | clear liquid | 3 |
| 10 | "pure" | DOW Amberlite XAD4 | clear liquid | 4 |
| 11 | technical | DOW Amberlite XAD4 | clear liquid | 4 |
| 12 | "pure" | A-Norit SX Plus (carbon) | clear liquid | 3 |
| 13 | technical | A-Norit SX Plus (carbon) | clear liquid | 3 |

To the Additives:

S6-62 (pressed wires) is a heterogenous catalyst obtainable from BASF. S6-62 comprises high amounts of iron oxide (Fe$_2$O$_3$) and potassium oxide (K$_2$O) The catalyst has the form of extruded wires which have a thickness of 3 mm.

NIO is a nano iron oxide powder (Fe$_2$O$_3$) powder.

SiO$_2$ is silica gel 60 for chromatography (0.04-0.065 mm) from Supelco.

Ambersept 900 (water wet) is a strong base anion exchange resin, capacity 0.80 eq/L water content 66-75%, pH range 0-14

Selexsorb COS of BASF is a Al$_2$O$_3$ based catalyst for the removal of COS, CO$_2$, H$_2$S and CS$_2$, the Al$_2$O$_3$ content is greater 93%.

Amberlite XAD4 is a hydrophobic polyaromatic resin with a styrene-divinylbenzene matrix from DOW
20-60 mesh
~0.98 mL/g pore volume; 100 Å mean pore size
750 m$^2$/g surface area.

A-Norit SX Plus (carbon) is a powdered activated charcoal, internally porous microcrystalline, non-graphitic forms of carbon, obtainable from Norit
Methylene blue adsorption 20 g/100 g
BET surf. area 1000 m$^2$/g (Total)
Bulk density 200-300 kg/m$^3$.

The invention claimed is:

1. A process for the purification of organic sulfur compounds, the process comprising:

contacting organic sulfur compounds in a liquid phase with an oxide of a metal from groups VIIb or VIIIb and an oxide of a metal from groups Ia to IIIa, or, alternatively, with a mixed-oxide thereof; for a contact period of at least 1 minute, and separating the oxide of a metal from groups VIIb or VIIIb and the oxide of a metal from groups Ia to IIIa, or the mixed-oxide, from the organic sulfur compounds, wherein the organic sulfur compounds are compounds of formula (I):

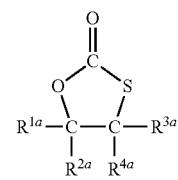

with $R^{1a}$ to $R^{4a}$ independently from each other representing hydrogen or an organic group with up to 50 carbon atoms, whereby, alternatively, $R^{2a}$, $R^{4a}$ and the carbon atoms to which they are attached together form a five to ten membered carbon ring; or compounds of formula (II):

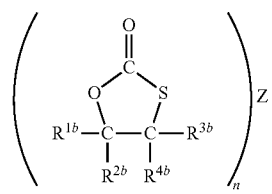

with $R^{1b}$ to $R^{4b}$ independently from each other representing hydrogen or an organic group with up to 50 carbon atoms, whereby, alternatively, $R^{2b}$, $R^{4b}$, and the carbon atoms to which they are attached together form a five to ten membered carbon ring, and one of the groups $R^{1b}$ to $R^{4b}$ is a linking group to Z, n representing an integral number of at least 2, and Z representing a n-valent organic group; or a mixture thereof.

2. The process according to claim 1, wherein the organic sulfur compounds are obtained as a product from a process comprising:

reacting a compound having at least one epoxy group or at least one halohydrin group with phosgene or an alkylformate, to give an adduct, reacting the adduct with a compound comprising anionic sulfur, to obtain a crude product, and optionally, further working-up the obtained crude product by extraction or distillation.

3. The process according to claim 1, wherein the oxide of a metal from groups VIIb or VIIIb is iron oxide.

4. The process according to claim 1, wherein the oxide of a metal from groups Ia to Ma is sodium oxide or potassium oxide.

5. The process according to claim 1, which is operated as a batch process.

6. The process according to claim 5, wherein the oxide of a metal from groups VIIb or VIIIb and the oxide of a metal from groups Ia to IIIa, or the mixed-oxide, is used in a total amount of 0.05 to 1 part by weight per 1 part by weight of the organic sulfur compounds.

7. The process according to claim 1, wherein the contacting of the oxide of a metal from groups VIIb or VIIIb and the oxide of a metal from groups Ia to IIIa, or the mixed-oxide, and the organic sulfur compounds is at 10° C. to 150° C.

8. The process according to claim 1, wherein the contact period is from 5 minutes to 12 hours.

9. The process according to claim 1, wherein the organic sulfur compounds obtained by the process have reduced odor.

* * * * *